United States Patent [19]

LeVeen et al.

[11] 4,389,208

[45] Jun. 21, 1983

[54] CATHETER ADVANCER

[76] Inventors: Robert F. LeVeen, 312 Lombard St., Philadelphia, Pa. 19147; Eric G. LeVeen, 3-3 Woodlike Rd., Albany, N.Y. 12203

[21] Appl. No.: 204,630

[22] Filed: Nov. 6, 1980

[51] Int. Cl.³ ............................................ A61M 25/00
[52] U.S. Cl. ..................................... 604/95; 604/106
[58] Field of Search ........................................ 128/4–8, 128/348–350, 243–245, DIG. 9; 604/95, 106

[56] References Cited

U.S. PATENT DOCUMENTS

| 1,697,834 | 1/1929 | McArthur | 128/244 |
|---|---|---|---|
| 2,974,932 | 3/1961 | Xenis | 15/104.05 X |
| 3,334,629 | 8/1967 | Cohn | 128/325 |
| 3,485,237 | 12/1969 | Bedford | 128/768 |
| 3,495,586 | 2/1970 | Regenbogen | 128/243 X |
| 3,665,928 | 5/1972 | Del Guercio | 128/350 R |
| 3,895,636 | 7/1975 | Choy | 128/348 |
| 4,207,872 | 6/1980 | Meiri et al. | 128/4 |

FOREIGN PATENT DOCUMENTS 1278965  11/1961  France .......................... 128/349 R Primary Examiner—Dalton L. Truluck Attorney, Agent, or Firm—Brooks, Haidt, Haffner & Delahunty

[57] ABSTRACT

A tubular device for advancing a medical treatment or examination instrument in a tubular passageway and having a head portion with outwardly biassed, rearwardly extending, flexible legs and a tail portion with outwardly biassed, rearwardly extending, flexible legs. The head and tail portions are interconnected by a fluid extensible bellows, and alternate expansion and contraction of the bellows causes advance of the head and following motion by the tail, the legs engaging the passageway wall and permitting forward motion but preventing backward motion through the passageway. In one embodiment of the device the head and tail parts are generally cylindrical and relatively rigid. In another embodiment, the head and tail portions each has extensible bellows arranged within a deformable cage constituted by jointed, flexible legs arranged to project outwardly to engage the passageway wall when the bellows they surround is contracted. The actuating fluid can be air supplied and withdrawn through a flexible tube or tubes communicating with the bellows and advancing with the device.

3 Claims, 12 Drawing Figures

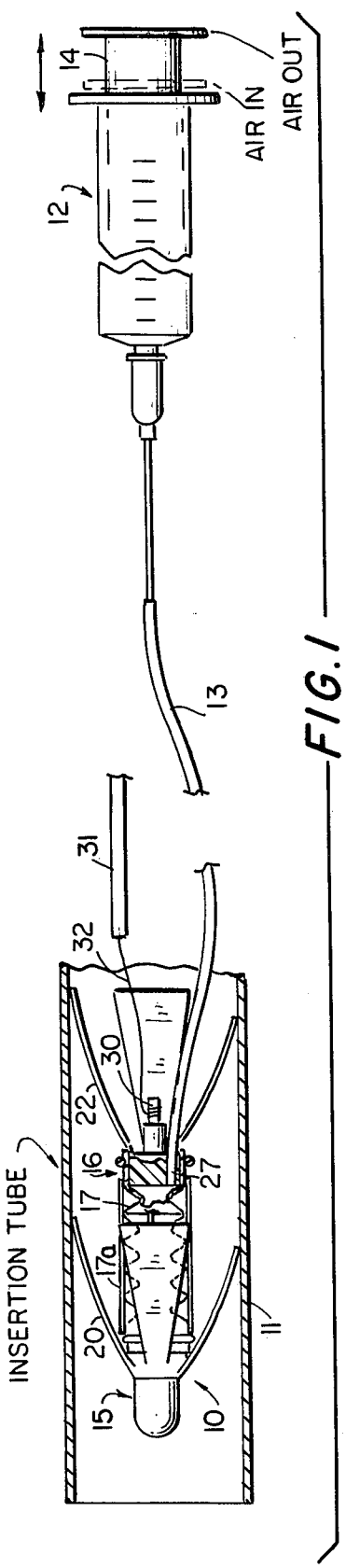
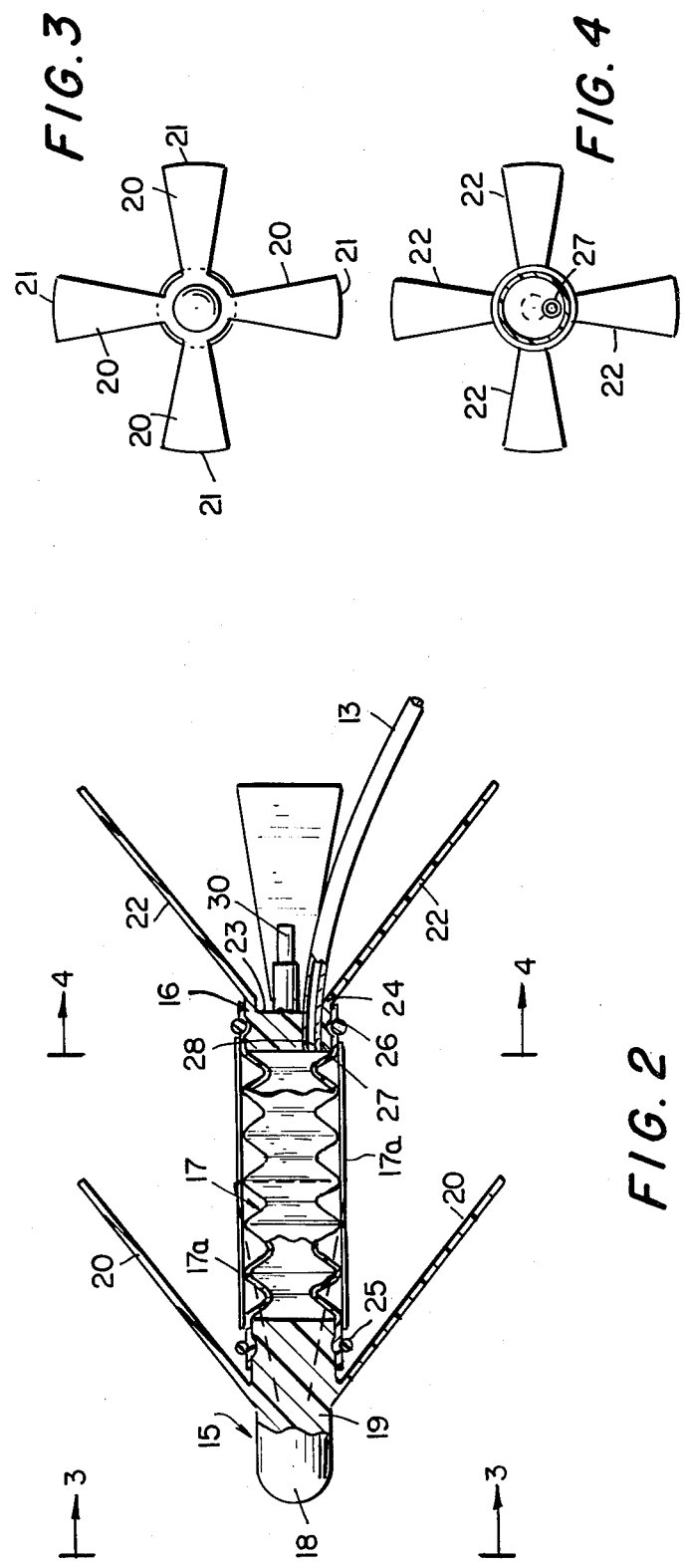
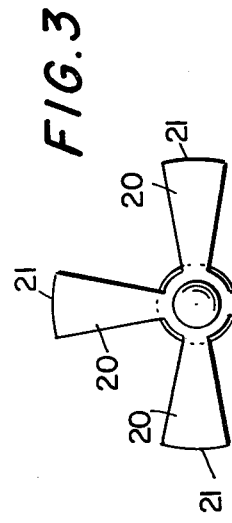
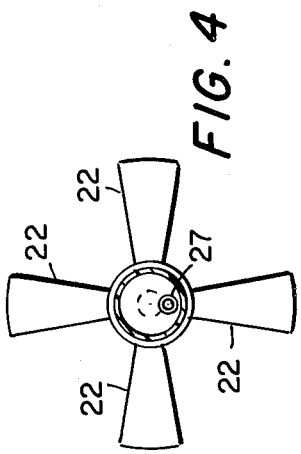

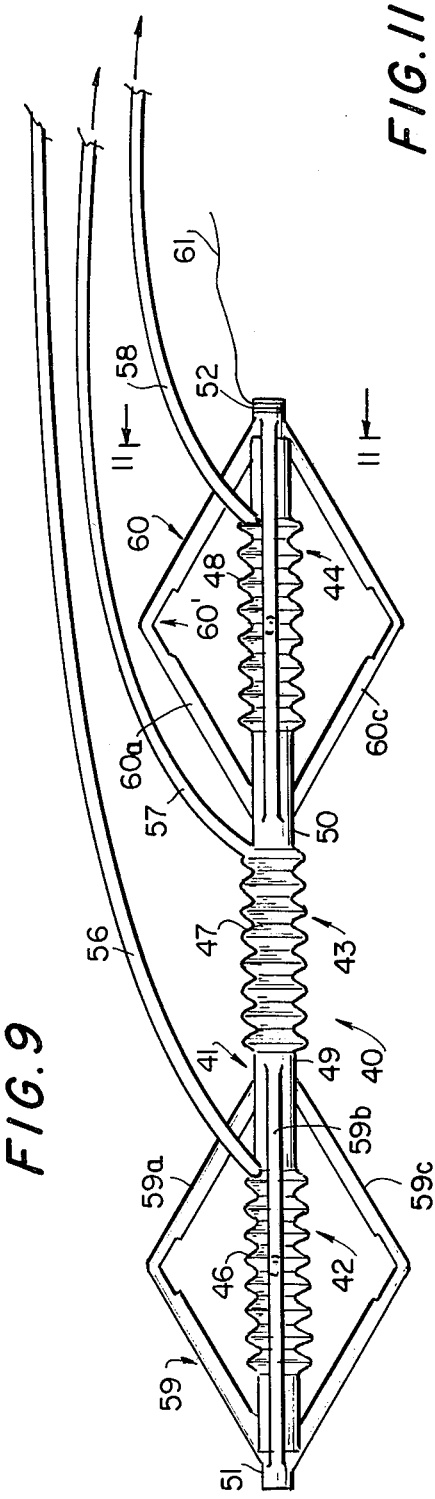
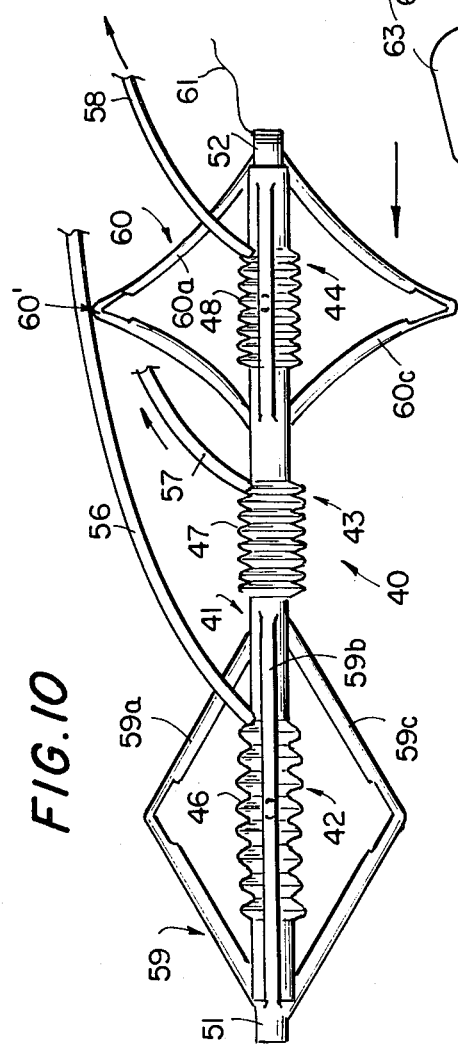
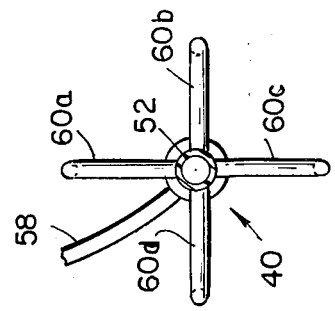
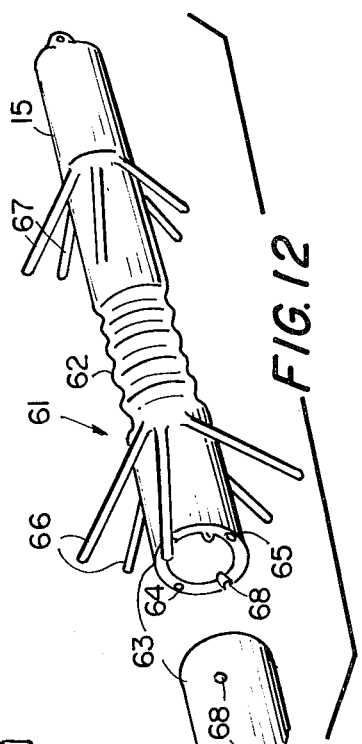

CATHETER ADVANCER

BACKGROUND OF THE INVENTION

1. Field of the Invention

The invention relates to movement along a tubular passage, and more particularly to a pressure actuated means for advancing an elongated flexible member.

2. Description of the Prior Art

Various medical procedures involve the oral or anal introduction of an implement such as an endoscope or drain into an internal body cavity, and the development of suitable fiber optics systems has greatly advanced the effectiveness of endoscopes. However there are difficulties in providing for insertion of elongated elements which must be sufficiently flexible to advance through irregular passages without damaging sensitive tissues yet rigid enough for external manipulation.

U.S. Pat. No. 4,148,307 describes a tubular medical instrument having at least three inflatable cuffs which are inflated in a sequence to move the instrument along a tubular passageway. The cuffs must be specially formed and must engage and distend the wall of the passageway. Furthermore, reliance is placed on substantial displacement of one cuff by another cuff which cannot always be assured, particularly if the wall of the passageway is relatively rigid. Furthermore, during forward movement of the instrument, the passageway is blocked by a cuff rearwardly of the head of the instrument which increases the gas pressure within the passageway if the forward end of the passageway is blocked.

U.S. Pat. No. 2,855,934 describes a similar tubular instrument with only two inflatable sleeves, corresponding to said cuffs, but requires a piston and cylinder assembly within the tube of the instrument. Such an assembly obstructs the tube undesirably and also creates a substantial length of rigid section in the instrument which increases the difficulty of moving the instrument around relatively sharp curves. The instrument is also objectionable because of the increase in gas pressure with forward movement.

A self-propelling, self-locating colonoscope has been described having a bellows intermediate a pair of inflatable bladders which have the objections of the sleeves or cuffs in said patents.

SUMMARY OF THE INVENTION

The present invention provides means for advancing a medical implement introduced anally or orally within the alimentary canal. Fluid, such as air is used to propel a device carrying the leading end of an implement along a tubular passage by alternating expansion and contraction of an extensible, preferably bellows-like, element sealingly connected to head and tail portions of the device which have outwardly extending means for permitting motion substantially only in one direction.

In one form of the device the head and tail portions are generally cylindrical, the head portion is weighted, and the tail portion has means for attachment of an implement to be drawn along by the device. The means permitting forward motion but preventing rearward motion are preferably a plurality of somewhat flexible, outwardly and rearwardly extending legs formed integrally with the head and tail portions respectively.

Another form of device according to the invention, which is presently preferred for medical procedures, has a central expansible and preferably bellows-like element for alternating expansion and contraction as in the embodiment just described, but in addition, the head and tail portions have longitudinally expansible and contractible, preferably bellows-like elements arranged within outwardly deformable cage-like structures comprising jointed, flexible members mounted for transverse extension, when the expansible member is contracted, for engagement with a passage wall. Successive expansion and contraction of the several expansible elements causes engagement of the tail portion, forward movement of the head portion, engagement of the head and disengagement of the tail portions and forward movement of the tail portion. Repetition of this cycle advances the device along a passage.

The device is preferably constructed of entirely non-toxic plastic and/or rubber materials. The actuating fluid, preferably air, is supplied to and withdrawn from the extensible element or elements through a flexible tube or tubes connected externally to a source of intermittent pressure such as a syringe.

For oral insertion of the device an insertion tube can be employed to guide the device into the esophagus.

These and other features and advantages of the invention will be more fully understood from the following detailed description of presently preferred embodiments of the invention, especially when that description is read in view of the accompanying figures of the drawings.

BRIEF DESCRIPTION OF THE DRAWINGS

In the drawings, in which like reference numerals designate like parts throughout:

FIG. 1 is an overall view, with parts broken away, of the catheter advancer of the invention, an insertion tube and a syringe;

FIG. 2 is a view, partly in section, of the catheter advancer of FIG. 1;

FIG. 3 is a view in section taken along line 3—3 of FIG. 2 and looking in the direction of the arrows;

FIG. 4 is a view similar to FIG. 3 taken along line 4—4 in FIG. 2;

FIG. 9 is a side view of another embodiment of the catheter advancer of the invention, with all expansible elements fully expanded;

FIG. 10 is a side view similar to that of FIG. 9 but with the central and rear extensible bellows in their contracted states;

FIG. 11 is an end view of the device of FIG. 9 taken along line 11—11 and looking in the direction of the arrows; and FIG. 12 is an isometric view of a modified form of the embodiment of the invention illustrated in FIGS. 1-8.

DETAILED DESCRIPTION OF PREFERRED EMBODIMENTS

Figure 5:
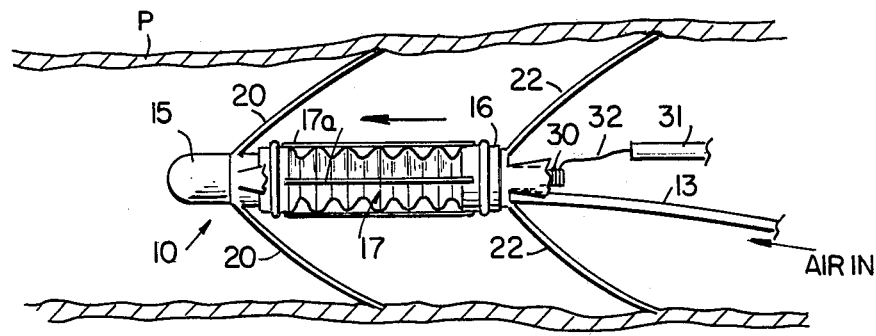
FIGS. 5, 6 and 7 illustrate in side view the manner of progress of the device of the invention along within a generally tubular body passage.

The overall view of FIG. 1 shows one embodiment of the advancement device of the invention generally designated by reference numeral 10 within an insertion tube 11 formed of somewhat flexible, non-toxic material. The device 10 is connected to a source of air under pressure, shown as an ordinary syringe 12, by a flexible tube 13, which can be a single lumen catheter. Air is forced to and away from the device 10 through the tube 13 by manipulation of the plunger 14 of the syringe 12.

The advancement device 10 is shown somewhat enlarged in FIG. 2. The size of the device 10 is determined by its intended use, so for use in adults the device 10 would be larger than a device intended for children, and a still smaller version might be used for infants. As illustrated in the drawings, the device 10 has a head portion 15 and a tail portion 16 interconnected by a longitudinally extensible, resilient body 17, preferably formed as a bellows as shown best in FIG. 2.

The head portion 15 has a rounded nose at 18 and a generally cylindrical body 19 from which a plurality (four shown) of somewhat flexible, biassed legs 20 extend outwardly and rearwardly at equally arcuately spaced locations. The legs 20 of the embodiment of FIGS. 1-8 preferably extend rearwardly at an angle of about 45 degrees to the axis of the cylindrical head portion 15 when in relaxed condition. The legs 20 may be pressed inwardly toward the axis of the device 10, but in such position, they are urged outwardly by reason of their own resilience. The legs preferably widen outwardly away from the body 19 as shown in FIG. 3, terminating in arcuately curved ends 21 for good engagement without damaging tissues. The head portion 15 and the legs 20 can be integrally formed of plastic material, or the legs can be separate members fitted in sockets of the head portion 15.

The rear or tail portion 16, as shown in FIG. 2, is also generally cylindrical, and preferably shorter and less massive than the head portion 15. The tail portion thus can have the general form of a thick disc. Legs 22, like the legs 20, extend from the tail portion 16 as shown best in FIGS. 2 and 4, and can be integrally formed with the tail portion 16 or jointedly attached thereto, to extend outwardly and rearwardly, preferably also at an angle of about 45 degrees, as in the case of the legs 20. It will be noted that the legs 22 join the rear portion 16 of the device at its rearmost part, and in the embodiment of the device illustrated in FIG. 2, the rear face 23 has a peripheral rearwardly projecting lip 24 from which the legs 22 extend.

The legs 20 and 22 are shown as flat and somewhat flexible for conforming to the internal area of a generally tubular passage for forward "crawling" motion. The legs 20 and 22 are sufficiently stiff to prevent rearward movement by their inclined relationship to the passage wall.

The extensible body 17 interconnecting the front portion 15 and the rear portion 16 is illustrated in the form of a bellows-like member formed of flexible sheet material and sealed in air-tight relation to the head and and tail portions 15 and 16. Such a bellow-like member has little radial expansion when inflated but extends axially when inflated. Such member also tends to contract, by reason of its resiliency, after air pressure therein is reduced. The bellows shape, with circumferential fold lines is preferred, but some other device which is air extensible along a line interconnecting the head portion 15 and the tail portion 16 can be employed to provide the actuation by alternating extension and contraction. The bellows-like member is shown held tightly and sealingly in place by means of rings 25 and 26 extending around the exterior of the bellows-like member 17 at the locations of cooperating annular grooves formed in the head and tail portions 15 and 16. The rings 25 and 26 can be elastic bands. Other air-tight sealing means such as adhesive seals can be used to interconnect the several members.

The bellows-like member 17, in operation, extends and contracts along its length, or axially, in response to increased or decreased internal fluid pressure, the actuating fluid being supplied and withdrawn from the interior of the element 17 by means of the flexible tube 13, which is shown having one end 27 opening through an aperture 28 in the rear portion 16 of the device 10 and secured in place at the aperture 28. The other end of the tube 13 is connected to a source of fluid under controlled intermittent pressure, such as the syringe 12 illustrated in FIG. 1 for actuation in the manner illustrated in FIGS. 5-7.

Figure 6:
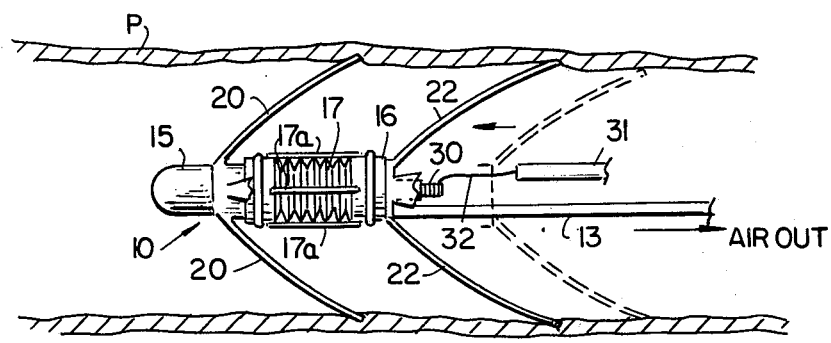

FIG. 5 illustrates the catheter advancer 10 in a generally tubular, but somewhat irregular passage such as a body cavity, with the legs 20 and 22 engaging the passage wall P. An insertion tube such as the tube 11 (FIG. 1) can be used to introduce the device 10 into such a body cavity, and it should be noted that although the irregularities in the wall P do not hinder advancement, such irregularities are not required for movement of the device along a passage, and the device will move effectively along a smooth-walled passage. The bellows-like interconnecting body 17 is shown extended in FIG. 5 by air under pressure introduced through the tube 13. FIG. 6 illustrates the condition which results when air is withdrawn from the bellows-like body 17, causing the body 17 to contract longitudinally, pulling the tail portion 16 forward in the direction shown by the arrow from the initial position shown by the dashed lines to an advanced position closer to the head portion 15, the engagement of the front legs 20 with the wall P preventing rearward movement.

Figure 7:
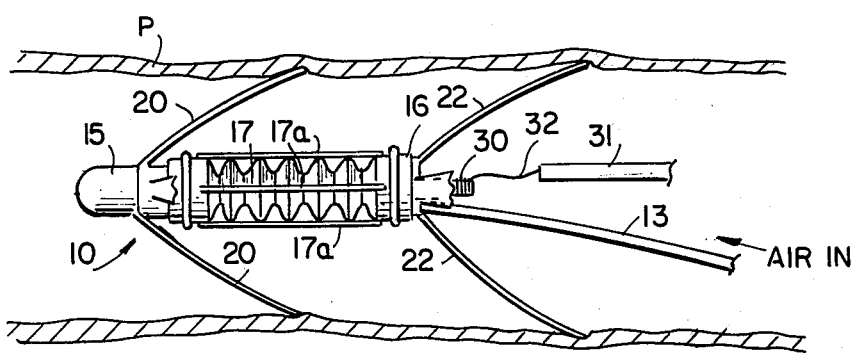

Air is then again injected into the bellows-like element 17 by way of the tube 13 and the head portion 15 is pushed forward by extension of the bellows-like body 17 as shown in FIG. 7, the engagement of the rear legs 22 with the wall P preventing rearward motion. By repeated expansion and contraction as illustrated, the device 10 is advanced stepwise in crawling movement through the passage.

In some cases the forward end of the passageway defined by the wall P may be blocked to the extent that either no fluids can exit therefrom or the fluids can exit therefrom only slowly. If the advancing device is large enough in diameter to fill or substantially fill the passageway or if it includes means which forms a fluid seal rearwardly of a portion thereof which advances, any fluid between the forward end of the passageway and the device or such a seal will be put under pressure when the device, or such portion, is advanced. If the passageway is in an animal part, such as the colon, such pressure can cause pain to the animal. It will be observed that the body 17 has a diameter smaller than the diameter of the passageway, and hence, smaller than the diameter of a circle containing the outer ends of the legs 20 and 22 when such are in the uncompressed state. Furthermore, it will be observed from the foregoing description of the operation of the device 10 that no fluid seal is formed at any time between the device 10 and the wall P. Thus, the device of the invention does not cause an increase of fluid pressure in the passageway during its advance.

Reverting to FIGS. 1 and 2, it will be seen that an article attachment means shown as a connecting post 30 extends rearwardly from the tail portion 16 for securing to the device 10 an implement such as a catheter, drain, or endoscope, generally designated by reference numeral 31 and attached to the post 30 by means of a flexible thread 32. More than one implement can be attached and advanced by the device of the invention. The post 30 is preferably integrally formed with the tail portion 16 and located at the middle of a rear face of the rear portion 16 as shown, for which reason the aperture 28 in which the tube 13 is fitted is shown positioned somewhat off-center in FIG. 4, but the reverse arrangement could be employed with the tube 13 entering at a central location and the connecting post 30 or other suitable attachment means located off-center.

In the operation described, air is forced into and drawn out of the body 17. Since the body 17 is in the form of a resilient bellows-like member which will normally contract to the length shown on FIGS. 1 and 2, it may not be necessary to pull the air out of the body 17 to make it contract. Instead, it may be sufficient merely to reduce the air pressure in the body 17 by venting the air to the atmosphere. The restoring or contracting force on the body 17 may, if desired, be increased by securing resilient members 17a, such as rubber bands, at their respective ends, to the head portion 15 and the tail portion 16. However, such members 17a may not be necessary, and if the air is removed from the body 17 by suction, the restoring or contracting force of the body 17 may be small.

As previously indicated the dimensions of the device can be varied to suit different applications, but for example, a device 10 for advancement of an implement along a bowel passage having a diameter of 1.5 inches, can be sized to advance about 2 inches in each contraction-expansion cycle of the bellows-like member 17. In this example the overall length of the device 10 can be about 2.25 inches when fully contracted and 4.25 inches when fully extended. The legs 20 and 22 can have a length of about 1.1 inches and the head and tail portions can be about one-half inch in diameter giving the device a maximum diameter of about 2.2 inches in relaxed condition, so that the legs 20 and 22 must be somewhat bent or flexed within a 1.5 inch passage as shown in FIGS. 5–7, providing the desired gripping action to prevent rearward motion.

Figure 8:
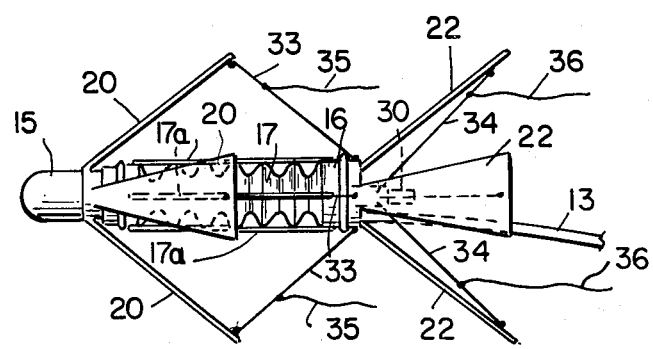
FIG. 8 is a side view of an embodiment of the device according to the invention showing retrieval means.

FIG. 8 illustrates one means for retrieval of the device 10, using an arrangement of retrieval strings connected to the legs 20 and 22 and extending back to the exterior of the passage into which the device has travelled. Strings 33 and 34 respectively connect the legs 20 and 22 to the tail portion 16 as shown in FIG. 8, and retrieval strings 35 and 36 serve to pull the legs 20 and 22 rearwardly and inwardly for withdrawal of the device 10 from a passage. An alternative manner of providing for retrieval of the device is to employ inflated members as the legs 20 and 22, keeping such legs inflated and firm during advancement and then deflating them and thereby decreasing the stiffness of the inflatable legs when it is desired to retrieve the device. Alternatively, and while not preferred, the legs 20 and 22 can be made flexible and soft enough to permit the device 10 to be withdrawn by pulling on the post 30 and without damage to the surrounding tube, the legs 20 and 22 bending sufficiently to permit such withdrawal. The head portion 15 of the device can be weighted by providing an insert of dense material (not illustrated) within the body 19 of the head portion 15 for extra weight, if desired.

Another embodiment of the advancer according to this invention is illustrated in FIGS. 9–11, in which the advancer device is generally designated by the reference numeral 40. The advancer 40 is intended for use in substantially the same manner as the device 10 of FIGS. 1–8, with or without an insertion tube like the tube 11, for advancing an elongated flexible member, for example, for advancing a catheter along and through a body cavity of a human or animal patient.

Like the device 10 of FIGS. 1–8, the advancer 40 of FIGS. 9–11, is dimensioned for its application and is preferably constructed in its entirety of non-toxic plastic and/or rubber materials. For various reasons, including ease of retrieval from a body cavity, the embodiment of FIGS. 9–11 is presently preferred for use in medical procedures.

The advancer 40 has a flexible elongated body 41 which is shown in a straight line conformation in FIGS. 9 and 10, but which can readily bend as required to follow the contour of a body cavity such as the intestine. This body 41 comprises three separate expansible portions or segments, a head portion 42, a middle portion 43, and a tail portion 44, each of which segments includes a longitudinally extensible, inflatable element, shown in the preferred form as a bellows with circumferential fold lines. Thus, the head portion is shown to include the bellows 46, the middle portion comprises bellows 47 and the tail portion includes the bellows 48. Each of the bellows elements is connected to a source of intermittently flowing actuating fluid, such as air under pressure, for expanding and contracting the several bellows 46, 47 and 48 independently of each other, the bellows being sealed off from each other by solid portions of the body 41 shown at 49 and 50, which solid portions can be generally cylindrical. Similar end portions 51 and 52 respectively seal the head end of the bellows 46 and the tail end of the bellows 48.

The supply of actuating air or other fluid under pressure to expand and contract the bellows elements 46, 47 and 48 can be a pump or pumps provided with suitable manual or automatically operable controls or valves remote from the device 40 and externally located with respect to a patient. In the drawing elongated flexible tubes 56, 57 and 58 are shown opening on to the bellows elements 46, 47 and 48 for supplying the bellows members with an intermittent supply of fluid under pressure to extend and contract the bellows members 46–48 in the proper sequence to advance or retract the device 40.

Instead of the rearwardly angled members 20 and 22 which serve as "legs" in the embodiment of the device 10 shown in FIGS. 1–8, the device of the invention illustrated in FIGS. 9–11 employs "legs" in the form of cage-like structures generally designated 59 and 60 and arranged about the head and tail portions 42 and 44 of the device 40 respectively so as to extend outwardly around the bellows members 46 and 48. The cage-like structures 59 and 60 are preferably integrally formed with the body 41 of the device 40, but of course, the device can be fabricated from individual parts attached together by adhesive or other suitable fastening means.

Each of the cage-like structures 59 and 60 is shown in FIGS. 9–11 to comprise four jointed, flexible leg members, designated by the reference numbers 59a–d and 60a–d respectively. Although the member 59d of the forward structure is not visible in the side views of FIGS. 9 and 10, the member 59d is disposed like the member 60d. All four elements of the rear cage-like structure 60 are seen in FIG. 11 to be arranged generally orthogonally with respect to each other. Cage-like structures comprising some number of jointed members other than four, for example, three such members disposed at angles of 120 degrees with respect to each other, or a number larger than four, could be employed, but the illustrated form having four jointed leg members forming the legs of each cage-like structure is presently preferred for stability and ease of fabrication.

Preferably, as in the embodiment first described, the legs of the members 59a–d and 60a–d are biassed outwardly by reason of their own resiliency so that in the fully contracted state of the relevant bellows, 46 or 49, the legs extend outwardly from the body 41 as shown in FIG. 9.

It will be seen that each of the jointed flexible members comprising the cage-like structures 59 and 60 extends outwardly in a V-shape from the body 41 of the device 40, the ends of the V-shapes of the members 59a through 59d being connected to the body 41 at the solid body portions 51 and 49 at opposite ends of the bellows 46, and the ends of the members 60a–60d being joined to the body 41 at the solid portions 50 and 52 at opposite ends of the tail bellows 48.

The apices or bent portions of the V-shaped members comprising the structures 59 and 60 are of reduced thickness as shown, for example at 60 in the member 60a of FIGS. 9 and 10, or otherwise formed so as to bend when the bellows members 46 and 48 expand or contract longitudinally, so that the jointed members 59a–59d and 60a–60d can move from the oblique angle configuration of FIG. 9 to the acute angle configuration of the structure 60 shown in FIG. 10, when the bellows members are contracted.

The advancer 40 of the embodiment of FIGS. 9–11 progresses along a generally tubular passage by sequential extension and contraction of the bellows members 42, 43 and 44 with consequent outward projection of the cage-like structures 59 and 60 upon longitudinal contraction of the respective associated bellows members 42 and 44 to engage the passage walls when the cage-like structures are in the configuration shown for the structure 60 in FIG. 10 and release from engagement when the bellows 46 and 48 are in their extended condition as illustrated at both the head and tail ends in FIG. 9 and at the head end of the device with structure 59 in FIG. 10. Not all of the several permutations of extended and contracted bellows members are illustrated in the drawings, since it is believed that they will be readily apparent from the illustrative conditions shown in FIGS. 9 and 10.

The illustration of FIG. 9 shows the device 40 with all bellows members 46–48 extended and the cage structures 59 and 60 accordingly in an obtuse angled condition, so they would not be firmly engaging walls of a generally tubular passage. Now, if the bellows 46 is contracted, by withdrawing fluid therefrom via the tube 56, the head portion 42 of the device will engage the passage walls by projection of the cage structure 59 into an acute angle condition of the jointed members 59a–59d. Then, leaving the bellows member 48 extended and the bellows member 46 contracted, the tail portion 44 of the bellows can be drawn forward by contraction of the middle bellows member 47 by withdrawing fluid therefrom via the tube 57. Then the rear bellows member 48 can be contracted to the condition shown in FIG. 10, causing the cage structure 60 to engage the passage walls, and the front bellows member 46 can be extended, releasing the passage walls by reducing the diameter of the cage structure 59 and causing the head of the device 40 to advance, as shown in FIG. 10. The head portion 42 will advance still further when the bellows member 47 is inflated while keeping the rear bellows 48 contracted. Repetition of this cycle will advance the device along the passage, whereas reversal of the sequence will produce movement in the earward direction. If desired, the device 40 can be withdrawn by expanding all of the bellows members to the condition of FIG. 9 and pulling the device backward.

Of course, it will be apparent that the advancer 40 may be moved in the forward direction or the rearward direction by a different sequence of operation of the bellows 46, 47 and 48. For example, with the bellows 46 extended, the bellows 48 is contracted and the bellows 47 is then extended thereby causing the head of the device 40 to move forward. Thereafter, the bellows 46 is contracted, the bellows 48 is extended and the bellows 47 is contracted to draw the cage 60 forward. The cycle may then be repeated to continue the forward advance and may be reversed to cause rearward movement.

An attachment filament 61 for securing a catheter, endoscope or other device is shown secured to the rear end 52 of the advancement device 40. The ends 52 and 51 of the device can of course be rounded or smooth like the front end 19 of the embodiment of FIGS. 1–8.

In the embodiment illustrated in FIGS. 1–8, the legs 20 and 22 increase in width in the direction from the ends thereof secured to the head and tail portions 15 and 16 to their free ends and a separate tube 13 is used to supply air to and remove air from the bellows-like member 17. If desired, the device 10 may be constructed as illustrated in FIG. 12.

In the embodiment illustrated in FIG. 12, the device 61 has a bellows-like member 62 sealed at its ends and connected at its opposite ends to a head portion 15 and to a tail portion 63 which is tubular. Air is supplied to and removed from the member 62 by way of passageways 64 and 65 in the wall of the tail portion 63. A plurality of legs 66, each of uniform size lengthwise, are secured to the tail portion 63 and correspond to the legs 22 shown in FIGS. 1–8. A plurality of similar legs 67 are secured to the head portion 15 and correspond to the legs 20 shown in FIGS. 1–8. The tail portion 63 may be provided with a plurality of holes 68 for irrigation or other purposes and may have a length at least equal to the maximum depth of insertion of the device 61 in a passageway. The operation of the device 61 is the same as the operation of the device 10.

Various other modifications, substitutions of parts or materials will suggest themselves to those acquainted with the art and such obvious changes are considered to be within the spirit and scope of the invention.

What is claimed is:

1. A device movable along and within a tubular passageway having a body comprising a head portion, a rear, tail portion and fluid extensible means extensible along a line interconnecting said head portion and said tail portion, said extensible means being connected intermediate said head portion and said tail portion for causing movement of one said portion toward the other said portion in the absence of fluid at a pressure in said means sufficient to extend said means and for causing movement of said one portion away from said other portion when fluid under pressure sufficient to extend said means is supplied thereto, said device further including fluid conduit means extending at least from said tail portion to said extensible means, a plurality of flexible, first legs on said head portion and extending outwardly thereof for engagement with the inner wall of said passageway, said first legs being secured at their head ends to said head portion in circumferentially different positions and having their opposite tail ends disposed rearwardly of their head ends, and a plurality of flexible, second legs on said tail portion and extending outwardly thereof for engagement with the inner wall of said passageway, said second legs being secured at their head ends to said tail portion in circumferentially different positions and having their opposite tail ends disposed rearwardly of their head ends, the tail ends of the legs on said head portion being connected to said body adjacent one end of said extensible means by flexible members, second fluid extensible means extensible in the same direction as said first-mentioned extensible means connected intermediate the head ends of said legs and the points of connection of said flexible members with said body, and second fluid conduit means extending from said second extensible means to at least said tail portion whereby the supply of fluid to said second extensible means through said second fluid conduit means causes the tail ends of said legs to move toward said body and the removal of fluid from said second extensible means causes the tail ends of said legs to move away from said body.

2. A device as set forth in claim 1 wherein the tail ends of the legs on the tail portion are connected to said body by flexible members and wherein there is a third extensible member between the head ends of the legs on said tail portion and the point of connection of the flexible members to said body and there is third fluid conduit means extending from said third extensible means to said tail portion, whereby the tail ends of the legs on said head portion and the tail ends of the legs on said tail portion may be separately moved toward and away from said body.

3. A device movable along and within a tubular passageway having a body comprising a head portion, a rear, tail portion and fluid extensible means extensible along a line interconnecting said head portion and said tail portion, said extensible means being connected intermediate said head portion and said tail portion for causing movement of one said portion toward the other said portion in the absence of fluid at a pressure in said means sufficient to extend said means and for causing movement of said one portion away from said other portion when fluid under pressure sufficient to extend said means is supplied thereto, said device further including fluid conduit means extending at least from said tail portion to said extensible means, a plurality of flexible, first legs on said head portion and extending outwardly thereof for engagement with the inner wall of said passageway, said first legs being secured at their head ends to said head portion in circumferentially different positions and having their opposite tail ends disposed rearwardly of their head ends, and a plurality of flexible, second legs on said tail portion and extending outwardly thereof for engagement with the inner wall of said passageway, said second legs being secured at their head ends to said tail portion in circumferentially different positions and having their opposite tail ends disposed rearwardly of their head ends, said extensible means being connected to said head portion by second extensible means and being connected to said tail by third extensible means, both the second extensible means and the third extensible means being extensible by fluid in the same direction as said first mentioned extensible means, and said device further comprising second fluid conduit means extending from said second extensible means to at least said tail portion, for supplying fluid to said second extensible means, third fluid conduit means extending from said third extensible means to at least said tail portion for supplying fluid to said third extensible means, first flexible members interconnecting the tail ends of said first legs with said body intermediate said first-mentioned extensible means and said second extensible means and second flexible members interconnecting the tail ends of said second legs with said body at the end of said third extensible means remote from said first-mentioned extensible means.

* * * * *